United States Patent
Lassila et al.

(10) Patent No.: US 6,288,151 B1
(45) Date of Patent: Sep. 11, 2001

(54) ALKYLATED AMINOALKYL CYCLIC UREA SURFACTANTS

(75) Inventors: Kevin Rodney Lassila, Macungie; Kristen Elaine Minnich; Richard Van Court Carr, both of Allentown, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/418,666

(22) Filed: Oct. 14, 1999

(51) Int. Cl.$^7$ .................................................. C08K 5/34
(52) U.S. Cl. ...................... 524/100; 544/316; 548/324.5
(58) Field of Search .................... 524/100; 548/324.5; 544/316

(56) References Cited

U.S. PATENT DOCUMENTS

| | | | |
|---|---|---|---|
| 2,787,619 | * 4/1957 | Yost | 260/309.7 |
| 2,840,546 | * 6/1958 | Yost | 260/77.5 |
| 2,840,561 | * 6/1958 | Yost | 260/256.4 |
| 2,840,566 | * 6/1958 | Yost | 260/309.7 |
| 3,876,657 | 4/1975 | Aelony et al. | 260/309.7 |
| 5,082,866 | * 1/1992 | Wong | 514/785 |
| 5,098,478 | 3/1992 | Krishman et al. | 106/23 |
| 5,562,762 | 10/1996 | Mrvos et al. | 106/22 |
| 5,691,369 | * 11/1997 | Pelosi | 514/392 |

OTHER PUBLICATIONS

J. Schwartz, "The Importance of Low Dynamic Surface Tension in Waterborne Coatings," *Journal of Coatings Technology*, Sep. 1992, vol. 64, pp. 65–74.

W. Wirth, S. Storp, and W. Jacobsen, "Mechanisms Controlling Leaf Retention of Agricultural Spray Solutions," *Pestic. Sci.*, 1991, vol. 33, pp. 411–420.

S. W. Medina and M. N. Stuovich, "Using Surfactants to Formulate VOC Compliant Waterbased Inks," *American Ink Maker*, 1994, vol. 72 (No. 2), pp. 32–38.

Nomura, et al., *Ind. Eng. Chem. Res.*, 1987, vol. 26, pp. 1056–1059.

Naumov, et al. (translated article published in *Khimiya Geteolikl. Soedin.* 1973, vol. 1, pp. 90–93), "N–Acyl and N–Alkyl–Substituted Ethyleneureas", pp. 79–82.

Kanetani, et al., *Nippon Kagaku Kaishi*, 1983, No. 1, pp. 107–111 (Chemical Abstracts, abstract#98:145450e).

Karol J. Mysels, "Improvements in the Maximum–Bubble–Pressure Method of Measuring Surface Tension", *Langmuir*, 1986, vol. 2, pp. 428–432.

* cited by examiner

Primary Examiner—Paul R. Michl
(74) Attorney, Agent, or Firm—Mary E. Bongiorno

(57) ABSTRACT

Novel alkyl aminoalkyl cyclic urea compounds of the structural formula:

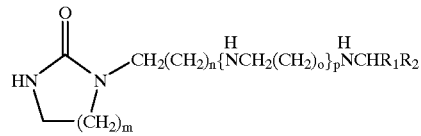

wherein each of m, n, and o are independently 1 or 2, p is 0 or 1, $R_1$ is $C_1$ to $C_4$ linear or branched alkyl, $R_2$ is $C_4$ to $C_{10}$ linear or branched alkyl, or, alternately, $CHR_1R_2$ forms a $C_6$ to $C_{12}$ substituted or unsubstituted cycloalkyl. These novel alkylated aminoalkyl cyclic ureas are useful as surfactants for reducing equilibrium and dynamic surface tension in water-based formulations, particularly coating, ink, and agricultural formulations.

24 Claims, No Drawings

ALKYLATED AMINOALKYL CYCLIC UREA SURFACTANTS

BACKGROUND OF THE INVENTION

The ability to reduce the surface tension of water is of great importance in waterborne coatings, inks, adhesives, and agricultural formulations because decreased surface tension translates into enhanced substrate wetting in actual formulations. Surface tension reduction in water-based systems is generally achieved through the addition of surfactants. Performance attributes resulting from the addition of surfactants include enhanced surface coverage, fewer defects, and more uniform distribution. Equilibrium surface tension performance is important when the system is at rest. However, the ability to reduce surface tension under dynamic conditions is of great importance in applications where high surface creation rates are utilized. Examples of such applications are spraying of coatings or agricultural formulations, and high speed gravure or ink-jet printing. Dynamic surface tension is a measure of the ability of a surfactant to reduce surface tension and provide wetting under such high speed application conditions.

Traditional nonionic surfactants such as alkylphenol or alcohol ethoxylates, and ethylene oxide (EO) propylene oxide (PO) copolymers have excellent equilibrium surface tension performance, but are generally characterized as having poor dynamic surface tension reduction. In contrast, certain anionic surfactants such as sodium dialkyl sulfosuccinates provide good dynamic results, but are very foamy and impart water sensitivity to the finished coating.

The importance of reducing equilibrium and dynamic surface tension in applications such as coatings, inks, and agricultural formulations is well-appreciated in the art. Low dynamic surface tension is particularly important in the application of waterborne coatings. An article by J. Schwartz, entitled "The Importance of Low Dynamic Surface Tension in Waterborne Coatings," in *Journal of Coatings Technology,* September 1992, vol. 64, pages 65–74, provides a discussion of surface tension properties in waterborne coatings. Equilibrium and dynamic surface tension are evaluated for several surface active agents. At a concentration of 0.1% in distilled water, the dynamic surface tension ranges from a low of about 32 to a high of 72 dynes per centimeter. It is pointed out that low dynamic surface tension is an important factor in achieving superior film formation in waterborne coatings. Dynamic coating application methods require surfactants with low dynamic surface tensions in order to prevent defects such as retraction, craters, and foam.

Efficient application of agricultural products is also highly dependent on the dynamic surface tension properties of the formulation. An article by W. Wirth, S. Storp, and W. Jacobsen, entitled "Mechanisms Controlling Leaf Retention of Agricultural Spray Solutions" in *Pestic. Sci.,*1991, vol. 33, pages 411–420, provides information on the relationship between the dynamic surface tension of agricultural formulations and the ability of these formulations to be retained on a leaf. These workers observed a good correlation between retention values and dynamic surface tension; i.e., more effective retention formulations exhibited low dynamic surface tension.

Low dynamic surface tension is also important in high-speed printing, as discussed in an article by S. W. Medina and M. N. Sutovich, entitled "Using Surfactants to Formulate VOC Compliant Waterbased Inks," in *American Ink Maker,* 1994, vol.72 (No.2), pages 32–38. The authors state that equilibrium surface tension (EST) is pertinent to ink systems at rest, but are not good indicators of performance in the dynamic, high speed printing environment under which the ink is used. Dynamic surface tension is reported as a more appropriate property. The dynamic measurement is an indicator of the ability of the surfactant to migrate to a newly created ink/substrate interface to provide wetting during high speed printing.

U.S. Pat. No. 5,098,478 (Krishnan, et al., 1992) discloses water-based ink compositions that have a dynamic surface tension of about 25 to 40 dynes/cm in order to reduce printability problems.

U.S. Pat. No. 5,562,762 (Mrvos, et al., 1996) discloses effective surfactants for jet inks. The inks, in which the surfactants are used, are reported to have a static surface tension of less than 40 dynes/cm and a dynamic surface tension of about 65 dynes/cm, and display cohesive ink placement during use.

A wide variety of substituted cyclic ureas are known. For example, Nomura et al., *Ind. Eng. Chem. Res.,* 1987, vol. 26, pages 1056–1059, disclose an effective catalyst for making cyclic ureas from carbonylation of diamines. The cyclic ureas are reported to be useful in a variety of applications; for example, as intermediates for medicines and resins, and as chemotherapeutic agents, delignification reagents, and in cosmetics.

U.S. Pat. No. 3,876,657 (Aelony et al., 1975) discloses preparation of 1-substituted-2-imidazolidinones. This class of compounds is recognized to have utility as bactericides, central nervous system depressants, plant growth promoters, female fly sterilants, adhesives, textile treating agents, and as monomers for deriving polymers and copolymers.

Naumov et al (translated article published in *Khimiya Geteotsikl. Soedin.* 1973, vol. 1, pages 90–93) disclose the synthesis of N-acyl and N-alkyl-substituted ethyleneurea. These materials are reported to be useful as biologically active compounds and many find practical application in pesticides.

Reports of alkylated aminoalkyl cyclic ureas are few and there are no known reports of alkylated aminoalkyl ureas having utility as surface tension reducing agents in water. In fact, Kanetani, et al., in *Nippon Kagaku Kaishi,* 1983, No.1, pages 107–111 (Chemical Abstracts, abstract # 98:145450e), disclose the conversion of N-alkylated aminoethylimidazolidinones to the propane sulfonic acid derivatives in order to make useful surfactants.

BRIEF SUMMARY OF THE INVENTION

This invention is directed to novel alkyl aminoalkyl cyclic urea compounds of the structural formula:

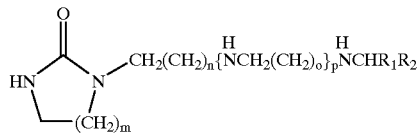

wherein m, n, and o are independently 1 or 2, p is 0 or 1, $R_1$ is $C_1$ to $C_4$ linear or branched alkyl, $R_2$ is $C_4$ to $C_{10}$ linear or branched alkyl, or, alternately, $CHR_1R_2$ forms a $C_6$ to $C_{12}$ substituted or unsubstituted cycloalkyl. These novel alkylated aminoalkyl cyclic urea compounds reduce equilibrium and dynamic surface tension in water-based formulations, particularly coating, ink, and agricultural formulations. It is desirable that an aqueous solution of the alkylated aminoalkyl cyclic urea demonstrates a dynamic surface tension of less than 45 dynes/cm at a concentration of 5 wt % or less in water at 23° C. and 1 bubble/second according to the maximum-bubble-pressure method. The maximum-bubble-pressure method of measuring surface tension is described in an article by Karol J. Mysels, *Langmuir*, 1986, vol. 2, pages 428–432.

This invention is also directed to a method of lowering equilibrium and dynamic surface tension of water-based formulations by incorporation of one or more of the above described alkyl aminoalkyl cyclic urea compounds.

This invention is also directed to a method for applying a water-based inorganic or organic compound-containing composition to a surface to partially or fully coat the surface with the water-based composition; wherein the water-based composition contains an effective amount of one or more alkyl aminoalkyl cyclic urea compounds of the above structure, for reducing the dynamic surface tension of the water-based composition.

There are significant advantages associated with the use of the novel alkyl aminoalkyl cyclic urea compounds in water-based coatings, inks, and agricultural formulations and these advantages include:

an ability to formulate water-borne coatings, inks, and agricultural formulations which may be applied to a variety of substrates with excellent wetting of substrate surfaces including contaminated and low energy surfaces;

an ability to provide a reduction in coating or printing defects such as orange peel and flow/leveling deficiencies;

an ability to produce water-borne coatings and inks which have low volatile organic content, thus making these surfactants environmentally favorable; and an ability to formulate coating and ink compositions capable of high speed application.

Because of their excellent surfactant properties and low foam characteristics, these novel compounds are likely to find applicability in applications in which reduction in dynamic and equilibrium surface tension and low foam are important. Such applications include various wet-processing textile operations, such as dyeing of fibers, fiber souring, and kier boiling, where low-foaming properties are particularly advantageous. They may also have applicability in soaps, water-based perfumes, shampoos, and various detergents where their marked ability to lower surface tension, and, at the same time, produce substantially no foam are highly desirable.

DETAILED DESCRIPTION OF THE INVENTION

The novel alkylated aminoalkyl cyclic urea compounds of this invention has the structure:

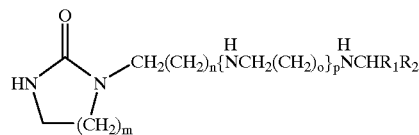

wherein m, n, and o are independently 1 or 2, p is 0 or 1, $R_1$ is $C_1$ to $C_4$ linear or branched alkyl, $R_2$ is $C_4$ to $C_{10}$ linear or branched alkyl, or, alternately, $CHR_1R_2$ forms a $C_6$ to $C_{12}$ substituted or unsubstituted cycloalkyl. Preferably, each of m and n is 1, p is 0, $R_1$ is methyl and $R_2$ is isoamyl. Compounds of this invention can be prepared by reacting an excess of a suitable polyamine with urea followed by recovery of the excess unreacted polyamine and reductive alkylation of the aminoalkyl cyclic urea with a suitable aldehyde or ketone.

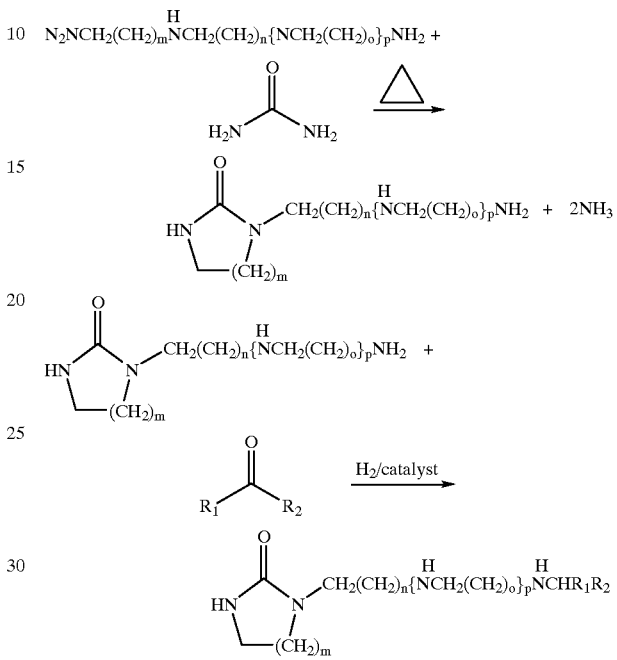

This is the preferred route for commercial production.

Examples of suitable $R_1$ alkyl groups are methyl, ethyl, propyl, n-butyl, isobutyl, sec-butyl, or tert-butyl. Examples of suitable $R_2$ alkyl groups are n-butyl, isobutyl, sec-butyl, tert-butyl, n-pentyl, isopentyl, hexyl, 2,2-dimethylbutyl, 2,3-dimethylbutyl, 2-ethylbutyl, heptyl, octyl, nonyl, decyl, and the like. Examples of the combination of $R_1$ and $R_2$, together with the carbon to which they are attached, are cyclohexyl, cyclooctyl, cyclodecyl, cyclododecyl, 4-ethylcyclohexyl, and the like.

In order to reduce the equilibrium and/or dynamic surface tension of a water-based, organic compound containing composition, an effective amount of one or more of the alkylated aminoalkyl cyclic urea compounds is added. Such effective amount can range from 0.001 to 20 g/100 mL, preferably 0.01 to 10 g/100 mL, of the water-based, organic compound containing composition. The most effective amount will depend on the particular application and the solubility of the particular alkylated aminoalkyl cyclic urea. In general, it is desirable that an aqueous solution of the alkylated aminoalkyl cyclic urea compound(s) demonstrates a dynamic surface tension of less than 45 dynes/cm at a concentration of about 5 wt % or less in water at 23° C. and 1 bubble/second according to the maximum-bubble-pressure method. The maximum-bubble-pressure method of measuring surface tension is described in an article by Karol J. Myers, *Langmuir*, 1986, vol. 2, pages 428–432.

A typical water-based coating formulation to which the alkylated aminoalkyl cyclic urea surfactants of the invention may be added comprise the following components in an aqueous medium at 30 to 80% solids:

| Typical Water-Based Coating Formulation | |
|---|---|
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvents |
| 0.01 to 10 wt % | Surfactant/Wetting Agent/Flow and Leveling Agents |
| 0.01 to 5 wt % | Alkylated aminoalkyl cyclic urea |

A typical water-based ink composition to which the alkylated aminoalkyl cyclic urea surfactants of the invention can be added comprise the following components in an aqueous medium at 20 to 60% solids:

| Typical Water-Based Ink Composition | |
|---|---|
| 1–50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-borne/water-dispersible/water-soluble resins |
| 0 to 30 wt % | Coalescing Solvents |
| 0.01 to 10 wt % | Surfactant/Wetting Agent |
| 0.01 to 10 wt % | Processing Aids/Defoamers/Solubilizing Agents |
| 0.01 to 5 wt % | Alkylated aminoalkyl cyclic urea |

A typical water-based agricultural composition to which the cyclic urea surfactants of the invention may be added would comprise the following components in an aqueous medium at 0.01 to 80% ingredients:

| Typical Water-Based Agricultural Composition | |
|---|---|
| 0.1–50 wt % | Pesticide or Plant Growth Modifying Agent |
| 0.01 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.01 to 20 wt % | Alkylated aminoalkyl cyclic urea |

EXAMPLE 1

This example illustrates the preparation of the reductive alkylation product of 2-(2-aminoethyl)imidazolidinone (AEI/MIAK) which has the following structure:

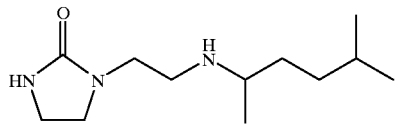

2-(2-aminoethyl)imidazolidinone (1.0 mole), methyl isoamyl ketone (0.85 mole) and 10% Pd/C (3.4 wt % of total charge) were charged to a one liter stainless steel autoclave. The reactor was sealed and purged with nitrogen then hydrogen. The contents of the reactor were heated to 90° C. under 7 bar (100 psig) $H_2$. The pressure was increased to 55 bar (800 psig) and maintained throughout the reaction by the admission of hydrogen from a 1 gallon (3.8 liters) ballast on demand by a dome regulator. The reactor contents were analyzed by GC/FID and found to be 77.2 area % monoalkylated (AEI/MIAK). The product was purified by distillation at 155–160° C., 0.8 millibar (0.6 Torr).

EXAMPLE 2

This example illustrates the preparation of 2-(2-aminoethyl-2-aminoethyl)imidazolidinone (AEAEI) by the reaction of triethylenetetraamine (TETA) with urea.

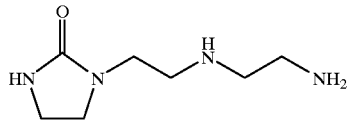

To 30 g (0.5 mole) of urea was added 292 g (2.0 mole) of triethylenetetraamine. The mixture was heated with stirring. Ammonia evolution began around 120° C. and the temperature was allowed to rise to 140° C. over a period of 1 hour and held there for an additional four hours. Unreacted TETA was removed at 0.13 millibar (0.1 torr) by a short path distillation. The crude product (71.9 g) was an off-white solid. An attempt to distill the AEAEI led to disproportionation. Therefore, the unpurified material was used in the making the compound of Example 3. The structure of AEAEI was verified using $^{13}C$ NMR analysis.

EXAMPLE 3

This example illustrates the preparation of the reductive alkylation product of AEAEI, from Example 2, with methyl isoamyl ketone (AEAEI/MIAK) which has the following structure:

AEAEI (0.15 mole), methyl isoamyl ketone (0.16 mole), methanol (206 mL) and 10% Pd/C (4 wt % of total charge) were charged to a one liter stainless steel autoclave. The reactor was sealed and purged with nitrogen then hydrogen. The contents of the reactor were heated to 90° C. under 7 bar (100 psig) $H_2$. The pressure was increased to 55 bar (800 psig) and maintained throughout the reaction by the admission of hydrogen from a 1 gallon ballast on demand by a dome regulator. The solvent was removed in vacuo and the unreacted methyl isoamyl ketone was removed by addition of water (50 g) followed by distillation at 60° C., 14 millibar (11 Torr) to remove the water/methyl isoamyl ketone azeotrope. The product was found to contain 8.5 wt % water by Karl Fischer analysis. The unpurified material was used in surface active studies.

EXAMPLE 4

This example illustrates the preparation of 3-aminopropylpropyleneurea (APPU) by the reaction of 3,3'-diaminopropylamine with urea. To 26.0 g (0.21 mole) of urea was added 142.7 g (1.09 mole) 3,3'-diaminopropylamine. The mixture was heated with stirring to 130° C. then to 140° C. over the next hour where it was maintained for an additional three hours. Excess 3,3'-diaminopropylamine was removed by a short path distillation at 75–80° C. and 1.3 millibar (1 torr). The white solid product was used without further purification in Example 5.

EXAMPLE 5

This example illustrates the preparation of the reductive alkylation product of APPU with methyl isobutyl ketone (APPU/MIBK) which has the following structure:

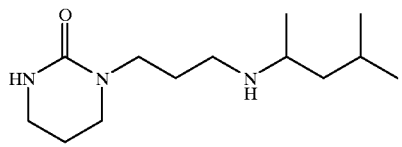

DAPAU (0.091 mole), methyl isobutyl ketone (0.1017 mole), methanol (208 mL) and 10% Pd/C (4 wt % of total charge) were charged to a one liter stainless steel autoclave. The reactor was sealed and purged with nitrogen then hydrogen. The contents of the reactor were heated to 80° C. under 7 bar (100 psig) $H_2$. The pressure was increased to 55 bar (800 psig) and maintained throughout the reaction by the admission of hydrogen from a 1 gallon (3.8 liters) ballast on demand by a dome regulator. The reactor contents were analyzed by GC/FID and found to be 85 area % monoalkylated DAPAU. Solvent and unreacted ketone were removed by rotary evaporation at 55° C. and 9 torr.

EXAMPLE 6

This example illustrates the preparation of the mixture 3-aminopropyl ethyleneurea (APEU) and 2-aminoethylpropyleneurea (AEPU) by the reaction of 3-aminopropylethylenediamine with urea. To 37.6 g (0.63 moles) of urea was added 298 g (2.55 moles) of 3-aminopropylethylenediamine. The mixture was heated with stirring to 120° C. then to 140° C. over the next hour where it was maintained for an additional 2.5 hours. Excess 3-aminopropylethylenediamine was removed by a short path distillation at 140° C. and 0.13 millibar (0.1 torr). The product was used without further purification in Example 7. GC/FID indicated that the product was a 1:1 mixture of APEU:AEPU.

EXAMPLE 7

This example illustrates the preparation of the reductive alkylation product of the APEU/AEPU mixture with methyl isobutyl ketone (APEU/MIBK and AEPU/MIBK mixture) which have the following structures:

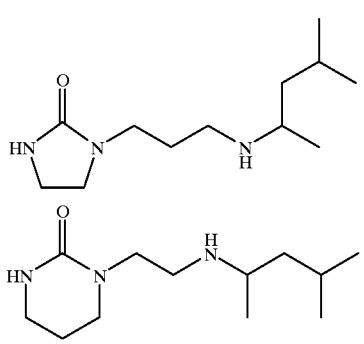

The APEU/AEPU mixture (0.185 mole), methyl isobutyl ketone (0.2021 mole), methanol (202 mL) and 10% Pd/C (4 wt % of total charge) were charged to a one liter stainless steel autoclave. The reactor was sealed and purged with nitrogen then hydrogen. The contents of the reactor were heated to 80° C. under 7 bar (100 psig) $H_2$. The pressure was increased to 55 bar (800 psig) and maintained throughout the reaction by the admission of hydrogen from a 1 gallon (3.8 liter) ballast on demand by a dome regulator. The reactor contents were analyzed by GC/FID and found to be 98 area % monoalkylated urea.

Comparative Example 8

Dynamic surface tension data were obtained for a 0.1 wt % aqueous solution of the 9.5 mole ethoxylate of nonylphenol using the maximum-bubble-pressure method at bubble rates from 0.1 bubbles/second (b/s) to 20 b/s. These data provide information about the performance of a surfactant at conditions from near-equilibrium (0.1 b/s) through extremely high surface creation rates (20 b/s). In practical terms, high bubble rates correspond to high printing speeds in lithographic or ink-jet printing, high spray or roller velocities in coating applications, and rapid application rates for agricultural products.

The data in Table 1 illustrate that for a conventional surfactant such as the 9.5 mole ethoxylate of nonylphenol, the surface tension at the low surface creation rate of 0.1 b/s is low (33.2 dyne/cm), but that the surface tension increases rapidly with surface creation rate to 56.2 dyne/cm at 20 b/s. These data indicate that this surfactant would not be suitable for use in high speed ink-jet or lithographic printing or rapid application of coatings or agricultural products.

TABLE 1

Dynamic Surface Tension for 9.5 mole Ethoxylate of Nonylphenol

| | Dynamic Surface Tension (dyne/cm) | | | | |
|---|---|---|---|---|---|
| concentration | 0.1 b/s | 1 b/s | 6 b/s | 15 b/s | 20 b/s |
| 0.1 wt % | 33.2 | 36.7 | 44.3 | 52.8 | 56.2 |

EXAMPLE 9

Aqueous solutions of AEI/MIAK were prepared and their surface tensions were measured using the procedure described in comparative example 8. The results are set forth in Table 2.

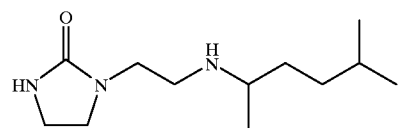

TABLE 2

Surface Tension Data for AEI/MIAK

| concentration | Dynamic Surface Tension (dyne/cm) | | | | |
|---|---|---|---|---|---|
| (wt %) | 0.1 b/s | 1 b/s | 6 b/s | 15 b/s | 20 b/s |
| 0.1 | 40.5 | 45.6 | 51.8 | 56.7 | 58.1 |
| 0.5 | 29.5 | 30.8 | 33.4 | 36.9 | 38.2 |
| 1.0 | 27.1 | 27.8 | 29.1 | 32.2 | 31.0 |
| 2.0 | 26.3 | 26.4 | 28.0 | 29.1 | 29.8 |

The data show that this material has an ability to reduce the surface tension of aqueous systems. At a use level of 0.5 wt % in water, the compound of this invention is able to provide a surface tension below 30 dyne/cm at 0.1 b/s, and maintain a surface tension well below 40 dyne/cm at 20 b/s. It has not previously been recognized that alkylated aminoalkyl imidazolidones would have the ability to reduce the surface tension of an aqueous system.

EXAMPLE 10

Aqueous solutions of AEAEI/MIAK were prepared and their surface tensions were measured using the procedure described in comparative example 8. The data are set forth in Table 3.

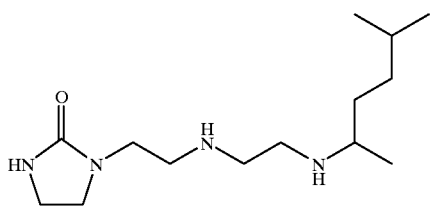

TABLE 3

Surface Tension Data for AEAEI/MIAK

| Concentration | Dynamic Surface Tension (dyne/cm) | | | | |
|---|---|---|---|---|---|
| (wt %) | 0.1 b/s | 1 b/s | 6 b/s | 15 b/s | 20 b/s |
| 0.09 | 42.6 | 53.4 | 57.8 | 60.7 | 61.3 |
| 0.46 | 29.9 | 33.4 | 40.7 | 46.2 | 47.0 |
| 0.91 | 28.0 | 29.8 | 35.6 | 40.0 | 40.1 |
| 4.56 | 25.7 | 25.9 | 26.6 | 28.1 | 28.9 |

These data illustrate that an additional aminoethyl link between the alkyl group and the cyclic urea leads to effective reduction of the surface tension of aqueous systems. Indeed, at a 0.46 wt % use level in water, the ability of this material to reduce surface tension is outstanding. The ability of these types of materials to reduce the surface tension of aqueous systems has not previously been recognized.

EXAMPLE 11

Aqueous solutions of APPU/MIBK were prepared and their surface tensions were measured using the procedure described in comparative example 8. The results are set forth in Table 4.

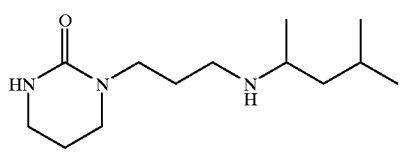

TABLE 4

Surface Tension Data for APPU/MIBK.

| Concentration | Dynamic Surface Tension (dyne/cm) | | | | |
|---|---|---|---|---|---|
| (wt %) | 0.1 b/s | 1 b/s | 6 b/s | 15 b/s | 20 b/s |
| 0.1 | 43.8 | 47.6 | 52.5 | 57.4 | 59.0 |
| 0.5 | 34.1 | 35.5 | 37.6 | 40.2 | 41.2 |
| 1.0 | 30.4 | 30.8 | 32.4 | 34.4 | 35.0 |
| 5.0 | 28.1 | 28.3 | 29.3 | 34.4 | 35.0 |

These data illustrate that alkylated aminoalkyl cyclic ureas incorporating a propyleneurea rather than an ethyleneurea would be useful in the practice of this invention.

EXAMPLE 12

Aqueous solutions of the APEU/MIBK and AEPU/MIBK mixture were prepared and their surface tensions were measured using the procedure described in comparative example 8. The results are set forth in Table 5.

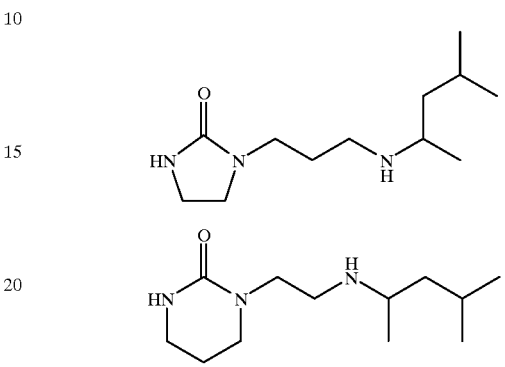

TABLE 5

Surface Tension Data for the APEU/MIBK and AEPU/MIBK mixture

| Concentration | Dynamic Surface Tension (dyne/cm) | | | | |
|---|---|---|---|---|---|
| (wt %) | 0.1 b/s | 1 b/s | 6 b/s | 15 b/s | 20 b/s |
| 0.1 | 59.3 | 60.4 | 60.7 | 62.0 | 62.5 |
| 0.5 | 47.6 | 48.4 | 49.6 | 51.4 | 52.1 |
| 1.0 | 37.2 | 42.6 | 44.5 | 46.3 | 47.0 |
| 5.0 | 31.0 | 31.6 | 32.2 | 34.7 | 34.8 |

These data illustrate that alkylated aminoalkyl cyclic ureas incorporating a mixture of propyleneurea and ethyleneurea moieties would be useful in the practice of this invention.

EXAMPLE 13

The foaming properties of 0.1 wt % solutions of N-octylpyrrolidinone, nonylphenol 9.5 mole ethoxylate, and several alkylated aminoalkyl cyclic urea surfactants of this invention were examined using a procedure based upon ASTM D 1173-53. In this test, a 0.1 wt % solution of the surfactant is added from an elevated foam pipette to a foam receiver containing the same solution. The foam height is measured at the completion of the addition ("Initial Foam Height") and the time required for the foam to dissipate at the air-liquid interface ("Time to 0 Foam") is recorded. This test provides a comparison between the foaming characteristics of various surfactant solutions. In general, in coatings, inks, and agricultural formulations, foam is undesirable because is complicates handling. Foam can also lead to coating and print defects and to inefficient application of agricultural materials. The results of the foam test are presented in Table 6.

TABLE 6
Foam Test Data
| Sample | Compound | Initial Foam Height (cm) | Time (sec) to 0 Foam or cm foam after 5 min |
|---|---|---|---|
| 1 | 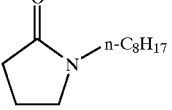 | 4.0 | 1.0 cm |
| 2 | nonylphenol 9.5 mole ethoxylate | 4.5 | 3.7 cm |
| 3 | 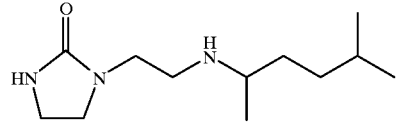 | 1.9 | 3 sec |
| 4 | 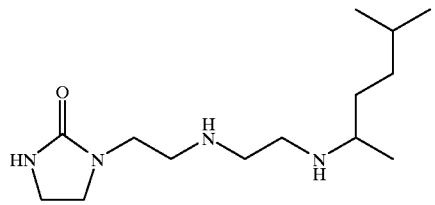 | 1.7 | 2 sec |
| 5 | 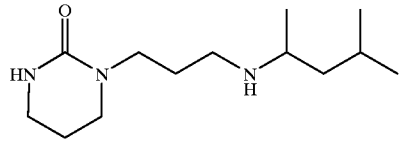 | 0.8 | 5 sec |
| 6 | mixture of 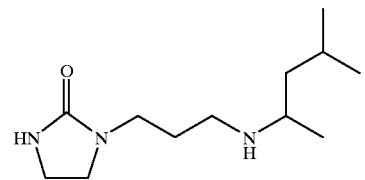 and 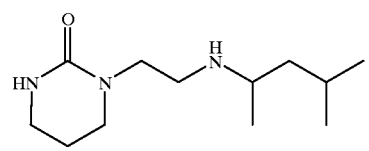 | 1.7 | 3 sec |

The data in Table 6 show that the known surfactants, n-octyl pyrrolidinone and 9.5 mole ethoxylate of nonylphenol (samples 1 and 2), produced a lot of foam, and the foam which formed was persistent; i.e., initial foam height was 4.0 and 4.5 cm, respectively, and foam height after 5 minutes was 1.0 and 3.7 cm, respectively. These materials would have limited applicability in coating, ink, and agricultural formulations. In contrast, the compounds of this invention (samples 3–6) produced very little foam and the foam dissipated quickly. Initial foam height was 0.8 to 1.9 cm which dissipated in 2 to 5 seconds. Thus, these materials have desirable properties with respect to their use in coatings, inks and agricultural formulations.

What is claimed is:

1. A composition having the structure

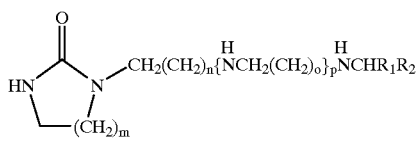

wherein each of m, n, and o are independently 1 or 2, p is 1, $R_1$ is $C_1$ to $C_4$ linear or branched alkyl, $R_2$ is $C_4$ to $C_{10}$ linear or branched alkyl, or, alternately, $CHR_1R_2$ forms a $C_6$ to $C_{12}$ substituted or unsubstituted cycloalkyl.

2. The composition of claim 1 wherein m and n are each 1.

3. The composition of claim 1 wherein m, n, and o are each 1, $R_1$ is methyl, and $R_2$ is isoamyl.

4. The composition of claim 1 wherein m and n are each 2.

5. The composition of claim 1 wherein o is 1, $R_1$ is methyl and $R_2$ is isobutyl.

6. A method for reducing the dynamic surface tension of an aqueous composition comprising an organic material or an inorganic material in water which comprises adding an effective amount of one or more alkylated aminoalkyl cyclic urea compounds for reducing the dynamic surface tension of the aqueous composition, wherein the one or more alkylated aminoalkyl cyclic urea compounds have the structure:

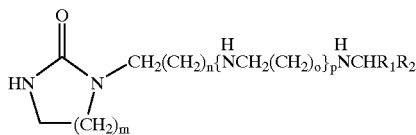

wherein each of m, n, and o are independently 1 or 2, p is 0 or 1, $R_1$ is $C_1$ to $C_4$ linear or branched alkyl, $R_2$ is $C_4$ to $C_{10}$ linear or branched alkyl, or, alternately, $CHR_1R_2$ forms a $C_6$ to $C_{12}$ substituted or unsubstituted cycloalkyl.

7. The method of claim 6 wherein the aqueous composition has a dynamic surface tension of less than 45 dynes/cm at a concentration of 5 wt % or less of the one or more alkylated aminoalkyl cyclic urea compounds in water at 23° C. and 1 bubble/second according to the maximum-bubble-pressure method.

8. The method of claim 6 wherein, in at least one of the one or more alkylated aminoalkyl cyclic urea compounds, m and n are each 1 and p is 0.

9. The method of claim 6 wherein, in at least one of the one or more alkylated aminoalkyl cyclic urea compounds, m and n are each 1, p is 0, and $R_1$ is methyl, and $R_2$ is isoamyl.

10. The method of claim 6 wherein, in at least one of the one or more alkylated aminoalkyl cyclic urea compounds, m and n are each 2, and p is 0.

11. The method of claim 6 wherein, in at least one of the one or more alkylated aminoalkyl cyclic urea compounds, m and n are each 2, p is 0 and $R_1$ is methyl and $R_2$ is isobutyl.

12. The method of claim 6 wherein, in at least one of the one or more alkylated aminoalkyl cyclic urea compounds, m, n, and p are each 1.

13. The method of claim 6 wherein the dynamic surface tension is at 20 bubbles/second.

14. The method of claim 6 wherein the aqueous composition is a coating composition comprising 20 to 80% components, said components comprising:

0 to 50 wt % pigment dispersant, grind resin, or mixtures thereof;

0 to 80 wt % coloring pigments, extender pigments, anti-corrosive pigments, other pigment types, or mixtures thereof;

5 to 99.9 wt % water-borne, water-dispersible, or water-soluble resins, or mixtures thereof;

0 to 30 wt % slip additives, antimicrobials, processing aids, defoamers, or mixtures thereof;

0 to 50 wt % coalescing or other solvents;

0.01 to 10 wt % surfactant, wetting agent, flow and leveling agents, or mixtures thereof; and 0.01 to 5 wt % one or more alkylated aminoalkyl cyclic urea compounds.

15. The method of claim 6 wherein the aqueous composition is an ink composition comprising 20 to 60% components, said components comprising:

1 to 50 wt % pigment;

0 to 50 wt % pigment dispersant, grind resin, or mixtures thereof;

0 to 50 wt % clay base in appropriate resin solution vehicle;

5 to 99.9 wt % water-borne, water-dispersible, or water-soluble resins, or mixtures thereof;

0 to 30 wt % coalescing solvent;

0.01 to 10 wt % surfactant or wetting agent or mixtures thereof;

0.01 to 10 wt % processing aids, defoamers, solubilizing agents, or mixtures thereof; and 0.01 to 5 wt % one or more alkylated aminoalkyl cyclic urea compounds.

16. The method of claim 6 wherein the aqueous composition is an agricultural composition comprising 0.01 to 80% ingredients, said ingredients comprising:

0.1–50 wt % pesticide or plant growth modifying agent, or mixtures thereof;

0.01 to 10 wt % surfactant;

0 to 5 wt % one or more dyes;

0 to 20 wt % thickeners, stabilizers, co-surfactants, gel inhibitors, defoamers, or mixtures thereof;

0 to 25 wt % antifreeze; and 0.01 to 20 wt % one or more alkylated aminoalkyl cyclic urea compounds.

17. In a method for applying a water-based composition to a surface in order to partially or fully coat the surface, wherein the water-based composition comprises an organic or inorganic compound and an effective amount of a surfactant for reducing the dynamic surface tension of the water-based composition, the improvement which comprises using a surfactant comprising one or more alkylated aminoalkyl cyclic urea compounds have the structure.

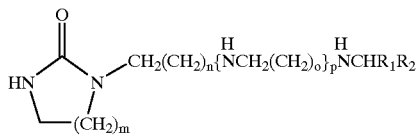

wherein each of m, n, and o are independently 1 or 2, p is 0 or 1 $R_1$ is $C_1$ linear or branched alkyl, $R_2$ is $C_4$ to $C_{10}$ linear or branched alkyl, or, alternately, $CHR_1R_2$ forms a $C_6$ to $C_{12}$ substituted or unsubstituted cycloalkyl.

18. The method of claim 17 wherein the aqueous composition has a dynamic surface tension of less than 45 dynes/cm at a concentration of 5 wt % or less of the one or more alkylated aminoalkyl cyclic urea compounds at 23° C. and 1 bubble/second according to the maximum-bubble-pressure method.

19. The method of claim 17 wherein, in at least one of the one or more alkylated aminoalkyl cyclic urea compounds m and n are each 1 and p is 0.

20. The method of claim 17 wherein, in at least one of the one or more alkylated aminoalkyl cyclic urea compounds, m and n are each 1, p is 0 and $R_1$ is methyl, and $R_2$ is isoamyl.

21. The method of claim 17 wherein, in at least one of the one or more alkylated aminoalkyl cyclic urea compounds, m and n are each 2, and p is 0.

22. The method of claim 17 wherein, in at least one of the one or more alkylated aminoalkyl cyclic urea compounds, m and n are each 2, p is 0 and $R_1$ is methyl and $R_2$ is isobutyl.

23. The method of claim 17 wherein, in at least one of the one or more alkylated aminoalkyl cyclic urea compounds, m, n, and p are each 1.

24. The method of claim 17 wherein the dynamic surface tension is at 20 bubbles/second.

* * * * *

UNITED STATES PATENT AND TRADEMARK OFFICE
CERTIFICATE OF CORRECTION

| | |
|---|---|
| PATENT NO. | : 6,288,151 B1 |
| DATED | : September 11, 2001 |
| INVENTOR(S) | : Kevin Rodney Lassila, Kristen Elaine Minnich and Richard Van Court Carr |

It is certified that error appears in the above-identified patent and that said Letters Patent is hereby corrected as shown below:

<u>Column 15,</u>
Line 9, delete "2,p is 0 or 1 $R_1$ is $C_1$ linear" and substitute therefore -- 2, p is 0 or 1, $R_1$ is $C_1$ to $C_4$ linear --.

Signed and Sealed this

Third Day of December, 2002

JAMES E. ROGAN
*Director of the United States Patent and Trademark Office*